(12) United States Patent
Moriarty et al.

(10) Patent No.: US 8,742,096 B2
(45) Date of Patent: Jun. 3, 2014

(54) METHODS AND COMPOSITIONS FOR PREPARING NORIBOGAINE FROM VOACANGINE

(75) Inventors: Robert M. Moriarty, Michiana Shores, CA (US); Simon Mbua Ngale Efange, Plymouth, MN (US)

(73) Assignee: DemeRx, Inc., Ft. Lauderdale, FL (US)

( * ) Notice: Subject to any disclaimer, the term of this patent is extended or adjusted under 35 U.S.C. 154(b) by 272 days.

(21) Appl. No.: 13/420,479

(22) Filed: Mar. 14, 2012

(65) Prior Publication Data

US 2012/0253037 A1  Oct. 4, 2012

Related U.S. Application Data

(60) Provisional application No. 61/468,515, filed on Mar. 28, 2011.

(51) Int. Cl.
*C07D 453/06* (2006.01)

(52) U.S. Cl.
USPC .......................................... 540/579

(58) Field of Classification Search
CPC ..................................... C07D 453/06
USPC .......................................... 540/579
See application file for complete search history.

(56) References Cited

U.S. PATENT DOCUMENTS

| | | |
|---|---|---|
| 2,813,873 A | 11/1957 | Janot et al. |
| 4,737,586 A | 4/1988 | Potier et al. |
| 6,211,360 B1 | 4/2001 | Glick et al. |
| 7,220,737 B1 | 5/2007 | Mash |
| 2003/0153552 A1 | 8/2003 | Mash et al. |
| 2010/0311722 A1 | 12/2010 | Mash |

OTHER PUBLICATIONS

International Search Report and Written Opinion dated Oct. 31, 2012 in related PCT Application No. PCT/US2012/030405.
Percheron et al., Ibogaine et vocangine. Compt. Rend. Acad. Sci., 245:1141-1143 (1957).

*Primary Examiner* — Brenda Coleman
(74) *Attorney, Agent, or Firm* — Foley & Lardner, LLP

(57) ABSTRACT

Disclosed are methods and compositions for preparing and purifying the non-addictive alkaloid noribogaine.

10 Claims, No Drawings

METHODS AND COMPOSITIONS FOR PREPARING NORIBOGAINE FROM VOACANGINE

FIELD OF THE INVENTION

This invention relates generally to methods and compositions for preparing and purifying the non-addictive alkaloid noribogaine.

STATE OF THE ART

Noribogaine is a well known member of the ibogaine family of alkaloids and is sometimes referred to as 12-hydroxyibogaine. U.S. Pat. No. 2,813,873 claims noribogaine albeit as "12-O-demethylibogaine" while providing an incorrect structural formula for ibogaine. The structure of noribogaine has now been thoroughly evaluated and is found to combine the features of tyrptamine, tetrahydrohavaine and indolazepines. Noribogaine can be depicted by the following formula:

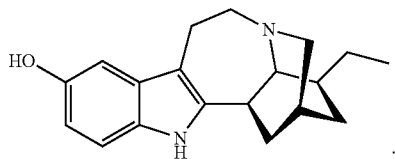

Noribogaine and its pharmaceutically acceptable salts have recently received significant attention as a non-addictive alkaloid useful in treating drug dependency (U.S. Pat. No. 6,348,456) and as a potent analgesic (U.S. Pat. No. 7,220,737).

Conventionally, noribogaine is prepared by demethylation of naturally occurring ibogaine:

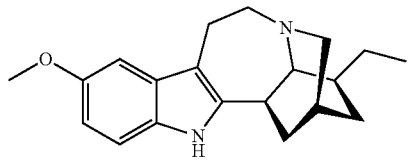

which is isolated from *Tabernanth iboga*, a shrub of West Africa. Demethylation may be accomplished by conventional techniques such as by reaction with boron tribromide/methylene chloride at room temperature followed by conventional purification. Alternatively, noribogaine can be prepared from the naturally occurring alkaloid, voacangine

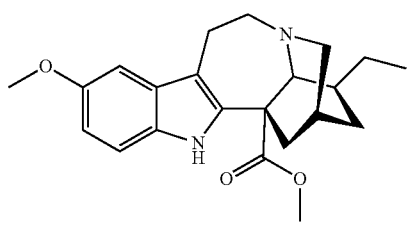

by decarboxylation followed by demethylation as described in U.S. Pat. No. 2,813,873. Such a process provides for ibogaine as the first intermediate in this two step synthesis.

Ibogaine is addictive and possesses hallucinogenic properties. It is a Schedule 1-controlled substance as provided by the US Food and Drug Administration. Accordingly, methods for preparing noribogaine from ibogaine require high levels of assurance that contamination with unacceptable levels of ibogaine is avoided. As above, a one-step method for preparation of noribogaine from ibogaine via demethylation does not provide the requisite assurance that ibogaine will consistently be removed as a potential contaminant. This applies equally as well to noribogaine prepared from voacangine as described above as the penultimate compound in this synthesis is ibogaine.

Accordingly, there is an ongoing need to provide a method for preparing noribogaine from voacangine such that the potential for ibogaine contamination can be effectively and reliably minimized.

SUMMARY OF THE INVENTION

This invention provides methods and compositions for the preparation of noribogaine wherein contamination by ibogaine is predictably and effectively minimized, if not altogether eliminated. In certain embodiments, this invention employs the use of solid supports to effect separation of noribogaine from any possible contaminants such that any ibogaine contamination is significantly reduced if not altogether eliminated. In certain embodiments, this invention employs an ion exchange resin to effect separation of noribogaine from any possible contaminants such that any ibogaine contamination is significantly reduced if not altogether eliminated.

Accordingly, in one of its method aspects, this invention is directed to a method for preparing noribogaine which method comprises:

a) converting voacangine to voacanginol, wherein the indole nitrogen is optionally protected by an amino protecting group;
b) optionally isolating the voacanginol or amino protected derivative thereof;
c) converting the voacanginol or amino protected derivative thereof to 12-hydroxy-voacanginol, wherein the indole nitrogen is optionally protected by an amino protecting group;
d) optionally isolating the 12-hydroxy-voacanginol or amino protected derivative thereof;
e) converting the product of step c) or d) to noribogaine; and
f) isolating noribogaine.

In another of its method aspects, this invention is directed to a method for preparing and purifying noribogaine which method comprises:

a) converting voacangine to voacanginol, wherein the indole nitrogen is optionally protected by an amino protecting group;
b) optionally isolating the voacanginol or amino protected derivative thereof;
c) converting the voacanginol or amino protected derivative thereof to a salt thereof, wherein the indole nitrogen is optionally protected by an amino protecting group;
d) optionally isolating the voacanginol salt or amino protected derivative thereof;
e) converting the voacanginol salt or amino protected derivative thereof to 12-hydroxy-voacanginol, wherein the indole nitrogen is optionally protected by an amino protecting group;
f) optionally isolating the 12-hydroxy-voacanginol or amino protected derivative thereof;

g) converting the product of step e) or f) to noribogaine; and
h) isolating noribogaine.

In another of its method aspects, this invention is directed to a method for preparing and purifying noribogaine which method comprises:
  a) converting voacangine to voacanginol, wherein the indole nitrogen is optionally protected by an amino protecting group;
  b) optionally isolating the voacanginol or amino protected derivative thereof;
  c) converting the voacanginol or amino protected derivative thereof to 12-hydroxy-voacanginol, wherein the indole nitrogen is optionally protected by an amino protecting group;
  d) optionally isolating the 12-hydroxy-voacanginol or amino protected derivative thereof;
  e) optionally covalently attaching 12-hydroxy-voacanginol or amino protected derivative thereof to a solid support via the 12-hydroxyl group of 12-hydroxy-voacanginol or amino protected derivative thereof so as to form a suspension of solid supports having 12-hydroxy-voacanginol or amino protected derivative thereof bound thereto;
  f) removing residual voacangine and/or voacanginol from said suspension;
  g) cleaving the covalent attachment and recovering the 12-hydroxy-voacanginol or amino protected derivative thereof from the solid support;
  h) converting the 12-hydroxy-voacanginol or amino protected derivative thereof to noribogaine; and
  i) isolating noribogaine.

In another of its method aspects, this invention is directed to a method for preparing and purifying noribogaine which method comprises:
  a) covalently attaching voacangine to a solid support via the indole nitrogen of voacangine so as to form a suspension of solid supports having voacangine bound thereto;
  b) converting voacangine to voacanginol under conditions wherein the level of voacangine bound to the solid support is less than 0.1 weight percent;
  c) converting the voacanginol to 12-hydroxy-voacanginol;
  c) cleaving and recovering 12-hydroxy-voacanginol from the solid support;
  d) converting the 12-hydroxy-voacanginol to noribogaine; and
  e) purifying noribogaine.

In another of its method aspects, this invention is directed to a method for preparing and purifying noribogaine which method comprises utilizing an ion exchange resin for isolating and/or purifying the voacanginol or salt thereof, 12-hydroxy-voacanginol or salt thereof, or noribogaine or a salt thereof.

In another of its method aspects, this invention is directed to a method for preparing and purifying 12-hydroxy-voacanginol wherein the indole nitrogen is optionally protected which method comprises:
  a) converting voacangine to voacanginol, wherein the indole nitrogen is optionally protected by an amino protecting group;
  b) optionally isolating the voacanginol or amino protected derivative thereof; and
  c) converting the voacanginol or amino protected derivative thereof to 12-hydroxy-voacanginol, wherein the indole nitrogen is optionally protected by an amino protecting group.

In one of its composition aspects, this invention is directed to a 12-hydroxy-voacanginol or salt thereof wherein said 12-hydroxy-voacanginol is optionally bound to an ion exchange resin.

In one of its composition aspects, this invention is directed to a solid support having voacanginol or salt thereof, 12-hydroxy-voacanginol or salt thereof which is covalently bound thereto through a cleavable linker.

DETAILED DESCRIPTION OF THE INVENTION

This invention is directed to methods and compositions comprising noribogaine and, in particular, methods and compositions comprising highly pure noribogaine. However, prior to describing this invention in greater detail, the following terms will first be defined.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a", "an", and "the" include plural referents unless the context clearly dictates otherwise. Thus, for example, reference to "a pharmaceutically acceptable excipient" includes a plurality of such excipients.

1. Definitions

Unless defined otherwise, all technical and scientific terms used herein have the same meaning as commonly understood by one of ordinary skill in the art to which this invention belongs. As used herein the following terms have the following meanings.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "about" when used before a numerical designation, e.g., temperature, time, amount, and concentration, including range, indicates approximations which may vary by (+) or (−) 10%, 5% or 1%.

As stated above, the invention is directed to compositions comprising noribogaine and an excipient to facilitate transport across the blood brain barrier.

As used herein, the term "noribogaine" refers to the compound:

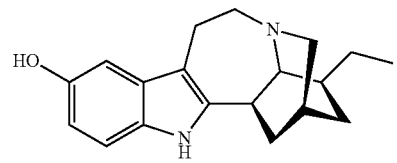

as well as its pharmaceutically acceptable salts thereof. Conventionally, noribogaine is prepared by demethylation of naturally occurring ibogaine:

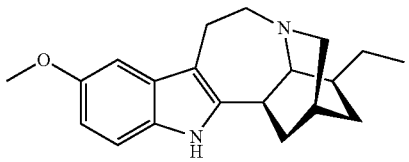

which is isolated from *Tabernanth iboga*, a shrub of West Africa. Demethylation may be accomplished by conventional techniques such as by reaction with boron tribromide/methylene chloride at room temperature followed by conventional purification. As disclosed herein, it is contemplated that noribogaine can be prepared essentially free of any potential ibogaine contamination from voacangine:

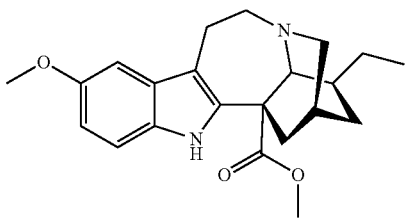

This invention is not limited to any particular chemical form of noribogaine and the drug may be given to patients either as a free base or as a pharmaceutically acceptable addition salt.

The term "voacanginol" refers to compounds of the formula:

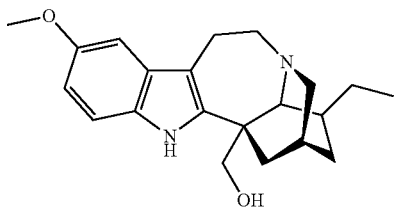

The term "voacanginol salt" refers to salts of the hydroxyl moiety of voacanginol. Exemplary salts include, but are not limited to, the lithium, sodium, and potassium salts.

The term "12-hydroxy-voacanginol" refers to a compound of the formula:

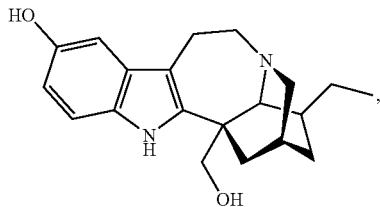

which can also be referred to as 12-O-desmethylvoacanginol.

The term "12-hydroxy-voacanginol salt" refers to salts of the hydroxyl moiety of voacanginol. Exemplary salts include, but are not limited to, the lithium, sodium, and potassium salts.

The term "solid support" refers to a material having a rigid or semi-rigid surface which contain or can be derivatized to contain reactive functionality which covalently links noribogaine or ibogaine to the surface thereof through a cleavable linker. Such materials are well known in the art and include, by way of example, silica, synthetic silicates, biogenic silicates, porous glass, hydrogels, silicate-containing minerals, synthetic polymers, polystyrene, polypropylene, polyacrylamide, polyethylene glycol, polyacrylamide and copolymers thereof including copolymers of polystyrene/polyethylene glycol and polyacrylamide/polyethylene glycol, and the like.

As used herein, the terms "cleavable linking arms" or "cleavable linker" refer to linking arms, which are a chemical group or a covalent bond which covalently attaches at one end to a solid support and at the other end to ibogaine or noribogaine. At least one of the covalent bonds of the linking arm which attaches ibogaine or noribogaine to the solid support can be readily broken by specific chemical or enzymatic reactions, thereby providing for ibogaine or noribogaine free of the solid support. The chemical or enzymatic reactions employed to break the covalent bond of the linking arm are selected so as to be specific for bond breakage thereby preventing unintended reactions occurring elsewhere on the compound. The cleavable linking group is selected relative to ibogaine/noribogaine formed on the solid support so as to prevent premature cleavage of either ibogaine or noribogaine from the solid support as well as not to interfere with any of the procedures employed during synthesis on the support. Suitable cleavable linking arms are well known in the art, and may include such groups as carbonate groups, carbamate groups, amide groups, and the like. In a preferred embodiment, the cleavable linker arm contains no more than 10 atoms. More preferably, the cleavable linker contains from 1 to 4 carbon atoms and from 2 to 4 heteroatoms selected from oxygen, nitrogen, sulfur, $S(O)$ and $S(O)_2$.

As used herein, the term "pharmaceutically acceptable salt" refers to pharmaceutically acceptable salts of noribogine which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

As used herein, the term "protecting group" or "Pg" refers to well known functional groups which, when bound to a functional group, render the resulting protected functional group inert to the reaction conditions to be conducted on other portions of the compound and which, at the appropriate time, can be reacted to regenerate the original functionality. The identity of the protecting group is not critical and is selected to be compatible with the remainder of the molecule. In one embodiment, the protecting group is an "amino protecting group" which protects the amino functionality of ibogaine or noribogaine during the reactions described herein. Examples of conventional amino protecting groups include, for instance, benzyl, acetyl, oxyacetyl, carboxybenzyl (Cbz), and the like. In another embodiment, the protecting group is a "hydroxy protecting group" which protects the hydroxyl functionality of noribogaine. Examples of hydroxylprotecting groups include, for instance, tosyl, benzyl, p-methoxybenzyl, p-nitrobenzyl, allyl, trityl, dialkylsilylethers, such as trialkylsilyl ethers such as trimethylsilyl ether, triethylsilyl ether, and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, benzyl, and p-nitrophenyl, methoxymethyl and tosyl. Additional examples of hydroxy protecting groups may be found in standard reference works such as Greene and Wuts, Protective Groups in Organic Synthesis, 2d Ed., 1991, John Wiley & Sons, and McOmie Protective Groups in Organic Chemistry, 1975, Plenum Press.

Preparation and Purification of Noribogaine

Voacangine (12-methoxyibogamine-18-carboxylic acid methyl ester) is an alkaloid found predominantly in the root-bark of the *Voacanga africana* tree, as well as in other plants such as *Tabernanthe iboga, Tabernaemontana africana, Trachelospermum jasminoides* and *Ervatamia yunnanensis*. Voacangine has been previously used as a precursor for the semi-synthesis of ibogaine (see U.S. Pat. No. 2,813,873).

The present application contemplates methods for preparing noribogaine from voacangine without providing ibogaine as an intermediate. Such methods are useful for a number of reasons. First, the known methods for the preparation of noribogaine comprise demethylating ibogaine as the final step. This is unlikely to provide pure noribogaine, and ibogaine contamination is undesirable as it is a schedule 1 controlled substance and is known to induce severe hallucinations. Second, ibogaine is isolated from the root of the *Tabernanthe iboga* and is therefore only a semi-renewable source as the plant must be compromised for isolation to take place, whereas voacangine is isolated from the bark and is thus renewable.

The compounds of this invention can be prepared using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Fourth Edition, Wiley, N.Y., 2007, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

It is contemplated that noribogaine can be prepared and/or purified from ibogaine by utilizing solid support as shown in the following Schemes, where PG represents an amine protecting group, LG represents a leaving group (e.g. a halo or alcohol), L represents a cleavable linking group (e.g. a carbonyl compound such as a carbonate or carbamate) and the shaded circle represents a solid support. In the following Schemes, the O-demethylation of the aryl methoxy group to provide the corresponding phenol can be accomplishing using any suitable method known in the art. Suitable reagents include protic acids such as HBr and HCl, a Lewis acid (e.g. $BBr_3$, $BCl_3$, $BF_3$, $AlCl_3$, etc.), a nucleophile (e.g. RS—, $N_3$—, $LiPPh_2$, SCN—), NaCN at low pH (e.g. pH 12), as well as L-Selectride, $NaN(SiMe_3)_2$, $LiN(^iPr)_2$, $SnO_2$, TMSI, iodocyclohexane in refluxing DMF, and the like. In some embodiments, the O-demethylation should be performed without converting the methyl ester to the corresponding carboxylic acid and/or without affecting the linkage to the solid support. Suitable reagents can be readily ascertained by one of skill in the art and can be found, for example, in T. W. Greene and G. M. Wuts, Protecting Groups in Organic Synthesis, Fourth Edition, Wiley, N.Y., 2007 (see, e.g., the reactivity charts at pages 1006-1008 and 1022-1032), and references cited therein.

Noribogaine 6 can be prepared and purified from voacangine 1 by the routes shown in Scheme 1.

Scheme 1

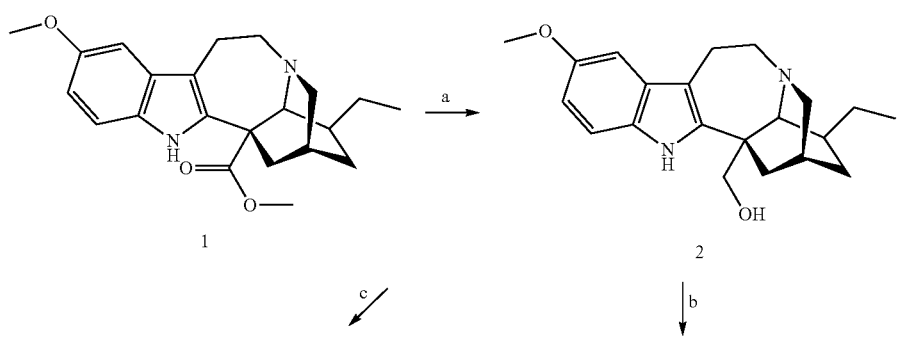

-continued

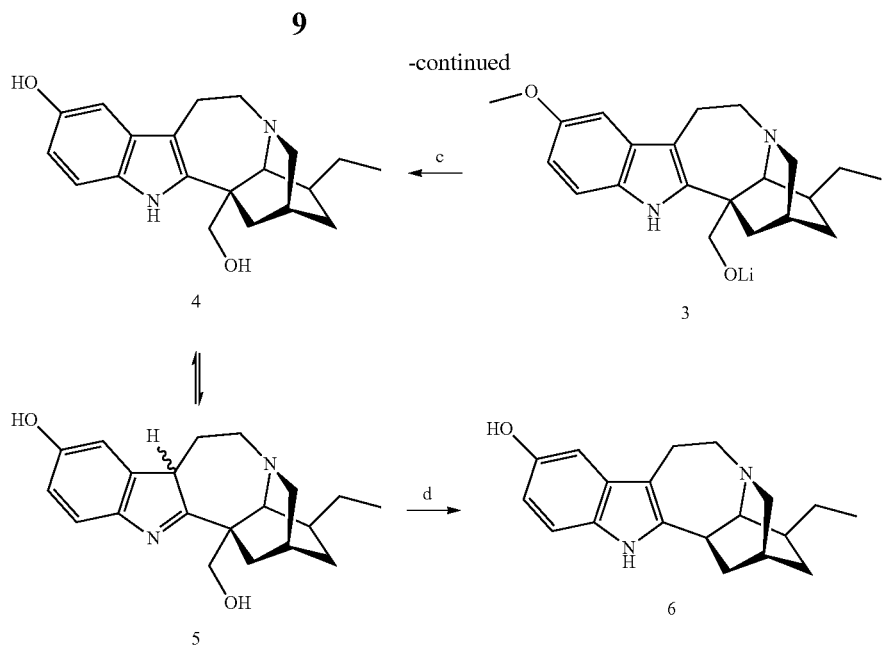

In one embodiment, provided herein is a method for preparing noribogaine 6, which method comprises reducing the 18-methyl ester functionality of voacangine 1 to provide the corresponding voacanginol 2. In some embodiments, the indole nitrogen can be optionally protected by an amino protecting group, such as tert-butoxycarbonyl or para-methoxy benzyl. The reduction of the 18-methyl ester functionality to provide the corresponding alcohol can be accomplishing using any suitable method known in the art, including, but not limited to, lithium aluminum hydride (LiAlH$_4$), sodium borohydride (NaH$_4$), and the like.

Subsequent conversion of the voacanginol 2 to 12-hydroxy-voacanginol 4 can optionally proceed via the voacanginol salt or amino protected derivative thereof. The salts can be formed from voacanginol 2 using a suitable base, such as n-butyl lithium, sodium metal, or sodium or potassium tert-butoxide. These steps can be performed in the same pot, or if desired, in two separate steps to facilitate purification. Any one or all of the voacanginol 2, 12-hydroxy-voacanginol salt 3, or 12-hydroxy-voacanginol 4, can be isolated and/or purified prior to the subsequent synthetic step.

Conversion of the voacanginol 2 to 12-hydroxy-voacanginol 4 can be accomplishing using any suitable method known in the art, including, but not limited to, protic acids such as HBr and HCl, a Lewis acid (e.g. BBr$_3$, BCl$_3$, BF$_3$, AlCl$_3$, etc.), a nucleophile (e.g. LiPPh$_2$, RS—, N$_3$—, SCN—), NaCN at low pH (e.g. pH 12), as well as L-Selectride, NaN(SiMe$_3$)$_2$, LiN($^i$Pr)$_2$, SnO$_2$, TMSI, iodocyclohexane in refluxing DMF, and the like. A subsequent retro-aldol step (typically performed using heat, see, Percheron et al., Compt. Rend. Acad. Sci. 245: 1141 (1957)) provides noribogaine.

The above steps can be performed in the same pot, or if desired, in separate steps to facilitate purification. Each of compounds 2, 3 and 4 can be isolated and purified as compounds per se. The noribogaine 6 can be isolated as the fee base or a salt thereof, such as the hydrochloride or hydrobromide salt thereof. In one embodiment, the noribogaine is isolated as noribogaine hydrochloride. In another embodiment, the noribogaine is isolated as noribogaine hydrobromide. One of skill in the art could readily interchange the anion using conventional methods.

Purification

Noribogaine 6, as well as the various intermediates disclosed herein can be further purified using standard techniques known in the art, such as column chromatography, crystallization, solid support chemistry, ion exchange chromatography, and the like. Noribogaine 6, as well as intermediates 2, 3 and 4 (as prepared in Scheme 1) can be purified using solid support chemistry as is known by one of skill in the art. Methods for the purification of noribogaine using solid support chemistry is disclosed in U.S. Patent Application Nos. 61/436,511, 61/453,884 and 61/454,904, entitled Methods and Compositions for Preparing Noribogaine from Voacangine, filed on Jan. 26, 2011, Mar. 17, 2011 and Mar. 21, 2011, respectively, which are hereby incorporated by reference in their entirety.

Alternatively, the 12-hydroxy-voacanginol 4 can be purified in a solution by adjusting the pH of the solution such that the phenol moiety is deprotonated (i.e., pH>10), and using an ion exchange resin to bind the deprotonated 12-hydroxy-voacanginol. By washing the resin, any residual unreacted voacanginol 2 can be removed from the solution. By repeating this process as many times as necessary, and preferably no more than 5 times, it is contemplated that noribogaine 3 having no detectable amount of ibogaine (i.e. less than 100 ppt) can be prepared.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

Example 1

Synthesis of Noribogaine from Voacangine

Example 1 illustrates one method for the synthesis and purification of noribogaine from ibogaine which method follows Scheme 2, below.

Scheme 2

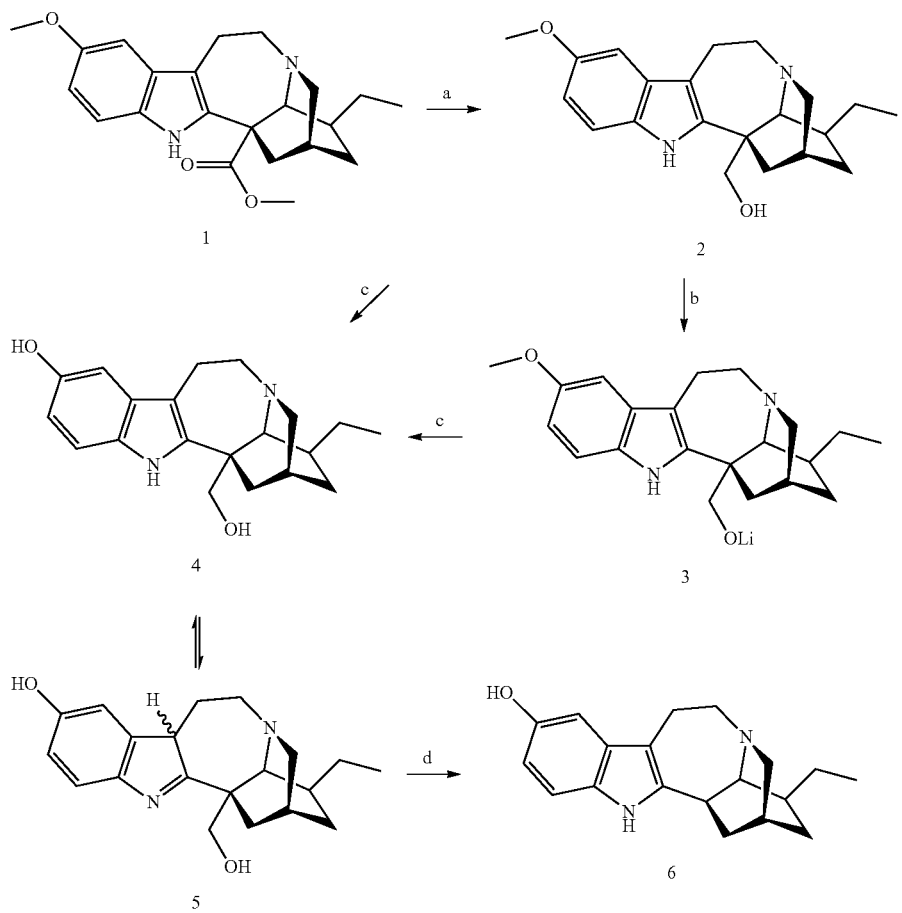

a: LiAlH₄; b: n-BuLi, THF or Na metal; c: i. BBr₃, CH₂Cl₂. ii. MeOH; d: heat

What is claimed is:

1. A method for preparing and purifying noribogaine which method comprises:
    a) converting voacangine to voacanginol, wherein the indole nitrogen is optionally protected by an amino protecting group;
    b) optionally isolating the voacanginol or amino protected derivative thereof;
    c) converting the voacanginol or amino protected derivative thereof to 12-hydroxy-voacanginol, wherein the indole nitrogen is optionally protected by an amino protecting group;
    d) optionally isolating the 12-hydroxy-voacanginol or amino protected derivative thereof;
    e) converting the product of step c) or d) to noribogaine; and
    f) isolating noribogaine.

2. A method for preparing and purifying noribogaine which method comprises:
    a) converting voacangine to voacanginol, wherein the indole nitrogen is optionally protected by an amino protecting group;
    b) optionally isolating the voacanginol or amino protected derivative thereof;
    c) converting the voacanginol or amino protected derivative thereof to a salt thereof, wherein the indole nitrogen is optionally protected by an amino protecting group;
    d) optionally isolating the voacanginol salt or amino protected derivative thereof;
    e) converting the voacanginol salt or amino protected derivative thereof to 12-hydroxy-voacanginol, wherein the indole nitrogen is optionally protected by an amino protecting group;
    f) optionally isolating the 12-hydroxy-voacanginol or amino protected derivative thereof;
    g) converting the product of step e) or f) to noribogaine; and
    h) isolating noribogaine.

3. A method for preparing and purifying noribogaine which method comprises:
    a) converting voacangine to voacanginol, wherein the indole nitrogen is optionally protected by an amino protecting group;
    b) optionally isolating the voacanginol or amino protected derivative thereof;
    c) converting the voacanginol or amino protected derivative thereof to 12-hydroxy-voacanginol, wherein the indole nitrogen is optionally protected by an amino protecting group;
    d) optionally isolating the 12-hydroxy-voacanginol or amino protected derivative thereof;
    e) optionally covalently attaching 12-hydroxy-voacanginol or amino protected derivative thereof to a solid support via the 12-hydroxyl group of 12-hydroxy-voacanginol or amino protected derivative thereof so as to form a suspension of solid supports having 12-hydroxy-voacanginol or amino protected derivative thereof bound thereto;

f) removing residual voacangine and/or voacanginol from said suspension;

g) cleaving the covalent attachment and recovering the 12-hydroxy-voacanginol or amino protected derivative thereof from the solid support;

h) converting the 12-hydroxy-voacanginol or amino protected derivative thereof to noribogaine; and i) isolating noribogaine.

4. A method for preparing and purifying noribogaine which method comprises:

a) covalently attaching voacangine to a solid support via the indole nitrogen of voacangine so as to form a suspension of solid supports having voacangine bound thereto;

b) converting voacangine to voacanginol under conditions wherein the level of voacangine bound to the solid support is less than 0.1 weight percent;

c) converting the voacanginol to 12-hydroxy-voacanginol;

c) cleaving and recovering 12-hydroxy-voacanginol from the solid support;

d) converting the 12-hydroxy-voacanginol to noribogaine; and e) purifying noribogaine.

5. The method for preparing and purifying noribogaine of claim 1, which method further comprises utilizing an ion exchange resin for isolating and/or purifying the voacanginol or salt thereof or the 12-hydroxy-voacanginol or salt thereof.

6. A solid support having voacanginol or voacanginol salt covalently bound thereto through a cleavable linker.

7. A solid support having 12-hydroxy-voacanginol or 12-hydroxy-voacanginol salt covalently bound thereto through a cleavable linker.

8. A compound of the formula:

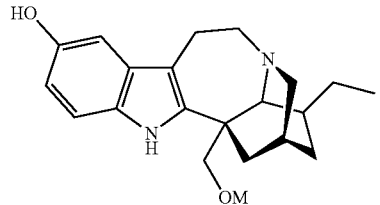

where M is lithium, sodium or potassium.

9. The compound of claim 8, wherein M is lithium.

10. A compound of the formula:

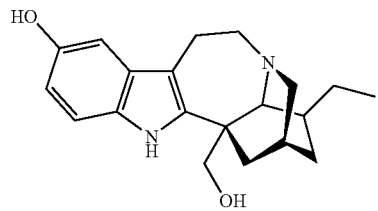

* * * * *